United States Patent
Lyman et al.

(10) Patent No.: US 6,790,655 B2
(45) Date of Patent: Sep. 14, 2004

(54) REMOVABLE SPLASH GUARDS FOR CULTURE PLATES

(75) Inventors: George F. Lyman, Kennebunk Port, ME (US); Joseph C. Wall, Southborough, MA (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 10/210,988

(22) Filed: Aug. 2, 2002

(65) Prior Publication Data

US 2003/0044971 A1 Mar. 6, 2003

Related U.S. Application Data

(60) Provisional application No. 60/309,914, filed on Aug. 3, 2001.

(51) Int. Cl.[7] .................................. C12M 1/22
(52) U.S. Cl. ................. 435/305.4; 435/288.3; 435/305.3; 215/232; 215/250; 215/253; 215/305
(58) Field of Search ................. 215/232, 250, 215/253, 305; 435/288.3, 288.4, 288.5, 304.1, 305.1–305.4

(56) References Cited

U.S. PATENT DOCUMENTS

| | | | |
|---|---|---|---|
| 3,307,602 A | 3/1967 | Boster | 150/5 |
| 4,034,853 A | * 7/1977 | Smith | 206/278 |
| 5,360,018 A | 11/1994 | Chen | 128/849 |
| 5,554,533 A | 9/1996 | Bedding et al. | 435/252.1 |
| 5,593,891 A | 1/1997 | Banes | 435/305.1 |
| 5,858,770 A | * 1/1999 | Perlman | 435/305.3 |
| 6,521,451 B2 | 2/2003 | Potter | 435/383 |

FOREIGN PATENT DOCUMENTS

DE      3218532 A1 * 11/1983

* cited by examiner

*Primary Examiner*—David A. Redding
(74) *Attorney, Agent, or Firm*—Vincent T. Kung

(57) ABSTRACT

A microorganism culture plate and methods for its fabrication and use is provided. The culture plate comprises a splash-guard that attaches to an upper rim of the plate. The splash-guard forms a removable, hermetic seal with the rim to prevent liquid media or other fluids from spilling or leaking out of the plate. The splash-guard as defined by a frame of film, according to an embodiment, has an aperture situated over a volume of the culture plate.

43 Claims, 4 Drawing Sheets

REMOVABLE SPLASH GUARDS FOR CULTURE PLATES

CLAIM OF PRIORITY

The present Application claims benefit of priority of U.S. Provisional Application No. 60/309,914, of the same title, filed on Aug. 3, 2001, the content of which is incorporated herein by reference.

TECHNICAL FIELD OF THE INVENTION

The present invention relates to cell culture dishes. In particular, the invention relates to splash-guards that are removable from the rim of cell culture dishes. Splash-guards are designed to prevent liquid media from spilling out of relatively shallow culture dishes during the preparation and handling processes.

BACKGROUND

The use of culture plates, traditionally known as Petri dishes or culture dishes, to grow or culture bacteria, eukaryotic cells, viruses, or other microorganisms has been long practiced. A typical culture dish or plate is made of a clear plastic structure, having a cylindrical, rectangular or square base with an open top and a complementary or mating lid, which is configured to rest on the base and close off the opening.

In normal use, a number of culture plates are assembled together at one time in a batch operation. Each culture plate is loaded with a desired liquid growth medium, similar in viscosity to water. The plates are placed on a larger tray, and the tray is moved, usually by hand, from location to location or into and out of an incubator. During this handling, the tray of culture plates may stick in the incubator rack and require force to dislodge it, or the tray may bump into the side or rear walls of the incubator, both of which exerts a jarring force on the culture plates. This jarring force, or simple movement during handling, often causes the liquid media within each culture plate to move, resulting in the liquid media sloshing about in the plate. Since culture plates typically are relatively shallow basins or containers with a short, surrounding sidewall of a height of about 10 mm to about 25 mm, and a large, open surface area, it is very difficult to prevent the liquid media from splashing onto the lid or inside-base sidewalls and/or over the top edge of the base sidewall during movement. When liquid travels to the outer, non-sterile areas of a culture plate, a path is created for bacteria growth to travel to the other inside areas of the culture plate and to contaminate the contents of the plate. Alternatively, media from inside the plate can splash out of the plate, down the outside sidewall and into the incubator environment. Obviously, such contamination is an unacceptable for use. Media leakage provides nutrients for bacteria of fungi to grow outside the culture plate and further contaminate the otherwise clean environment inside an incubator.

The same contamination problems discussed above occur when a user handles an individual culture plate. Mere movement of the individual culture plate results in the splashing of liquid media. Moreover, if the culture plate is growing or includes a pathogenic or radioactive material, or other dangerous specimens, it is highly undesirable for the material to splash out of the culture plate onto the user or into the outside environment.

Raising the edges of the culture plate to make the plate deeper would minimize the problem of liquids splashing out of the plate. This approach, however, would not be conducive to mass processing a number of plates together, since the trays and storage density in the incubator are made for culture plates of standardized width, length, and height. Some current designs of standard height incorporate a beveled baffle or inner rim at the top edge or along the inside of the sidewall of a culture plate, such as described in U.S. Pat. No. 5,593,891 issued to Albert J. Banes. Having its advantages, this second approach, however, can create other problems with contamination from capillary wicking of the liquid media and cells into inaccessible recesses of the plate. A molded baffle or frame that is attached with a seal to the base plate would be subject to viscous media seepage into the seal. Any cells in the media trapped between the baffle and plate would die and contaminate potentially the entire culture. Additionally, mechanically affixing or welding a non-removable frame of plastic to the inner rim of a culture plate will likely restrict access to cells for microscopic viewing or during harvesting. Moreover, these types of design likely have associated manufacturing difficulties due to their rather complex shapes.

Hence, an objective of the present invention is to provide an improved splash-guards for conventional culture dishes, in which the flow of liquid over the top of the base side wall is eliminated or greatly reduced for all but the most violent movement of the dish. Another objective of the present invention to provide a culture plate or modification of existing culture plates in an arrangement that is reliable, easy to use, and inexpensive to manufacture. The invention can provide culture dishes that are pre-fitted with the inventive splash-guard. Further, a removable splash-guard design is more advantageous, since it would permit users to have better access to the entire surface area of a culture plate.

SUMMARY OF THE INVENTION

The present invention comprises a culture plate having an open-ended basin or container with a bottom wall, at least one sidewall extending upwardly from the bottom wall, and a splash guard that is removably attached to a top edge or rim of the sidewall. The splash-guard defines a frame-like structure with an open, central aperture and inwardly extending flanges that cover the top edges of the side wall and a peripheral portion of the bottom wall. The splash-guard is made of semi-rigid materials, such as plastics. When attached to the edge, the splash-guard remains in a horizontal plane relative to the open-end or mouth of the plate and does not dip within the volume defined by the side wall(s) of the culture plate. The splash-guard can be easily pealed off of the top of the open-end of the plate basin, starting with a pull-tab located near one corner. The splash-guard is also workable with common lid configurations, since it can easily fit or fold under the lid when the culture plate is covered.

DETAILED DESCRIPTION OF THE INVENTION

Figure 1A:
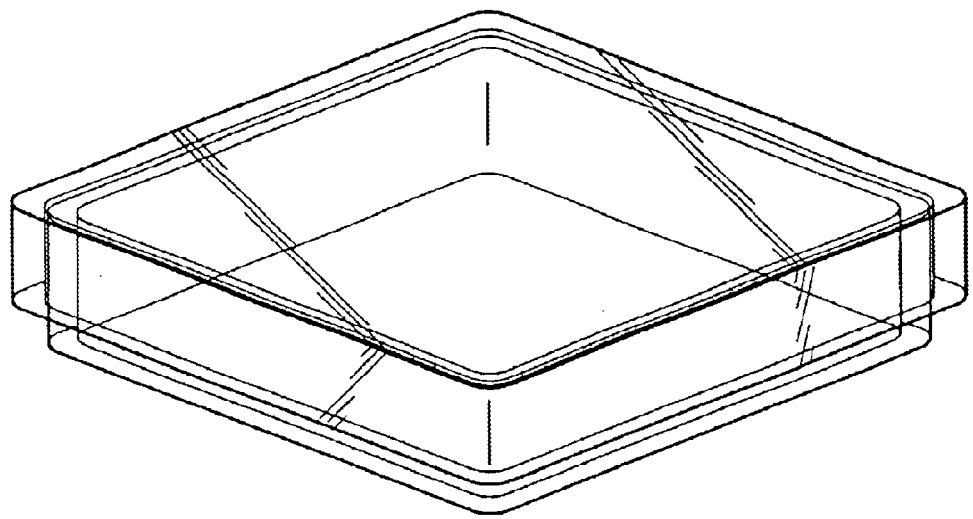
FIG. 1 shows a variety of cell culture dishes.
Figure 1B:
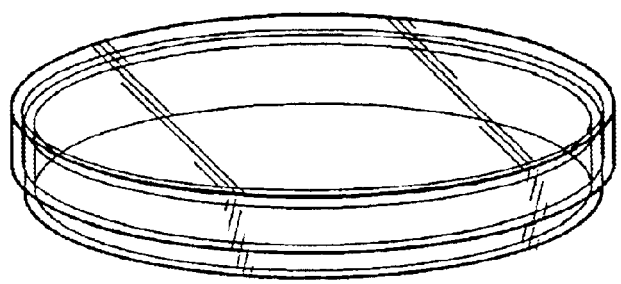

The present invention encompasses a splash-guard for cell culture plates. A typical culture plate, like that shown in FIG. 1, comprises a container with an open top, a bottom wall, and at least one side wall extending from the bottom wall to define or constitute a basin for accommodating liquids or other media for cell cultures. Liquid media loaded in a culture plate tend to splash or slosh about when the culture plate is moved or handled in normal use. A splash-guard retains fluid within the basin or container of the culture plate. Any liquid that splashes or slops up due to movement is prevent from spilling out of the culture dish, because the liquid hits the underside of the splash-guard film and is deflected back into the basin.

Figure 2:
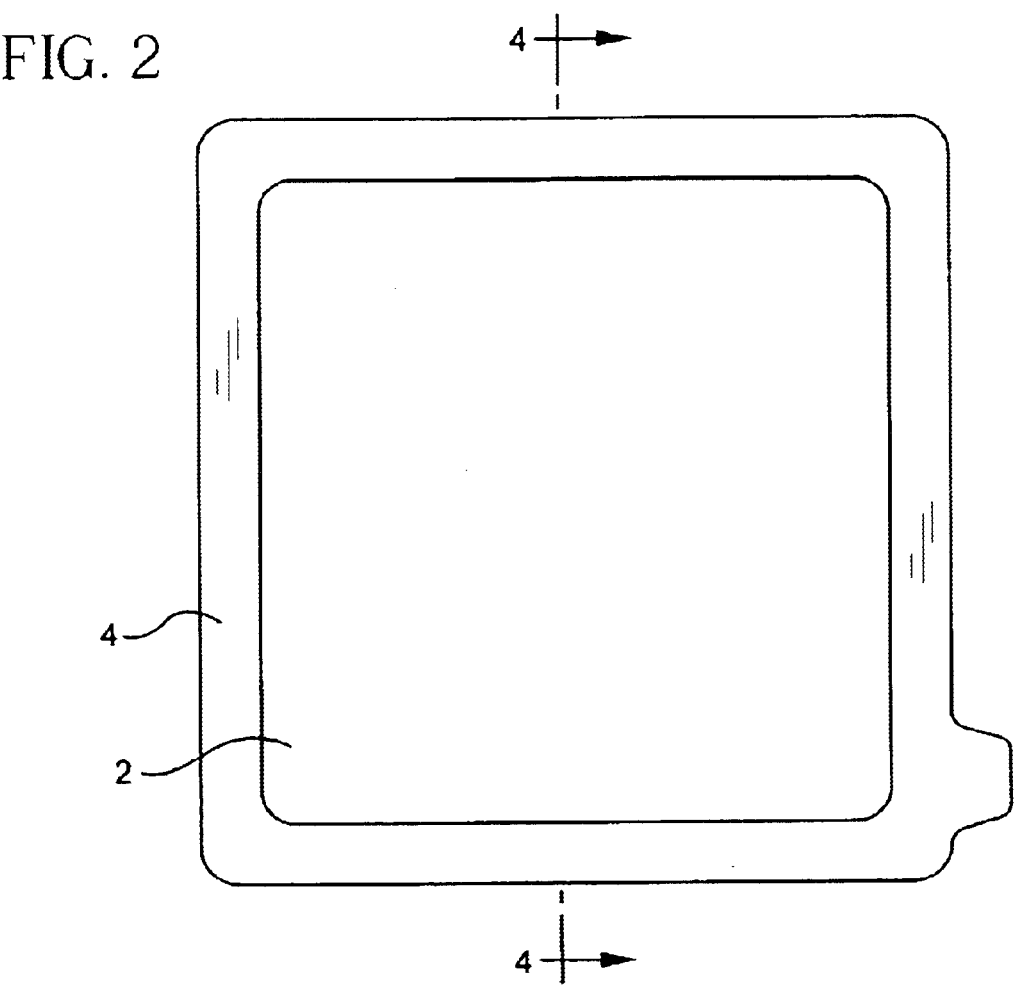
FIG. 2 shows a die cut shape frame of clear or translucent film for a square culture dish, according to one embodiment.
Figure 3:
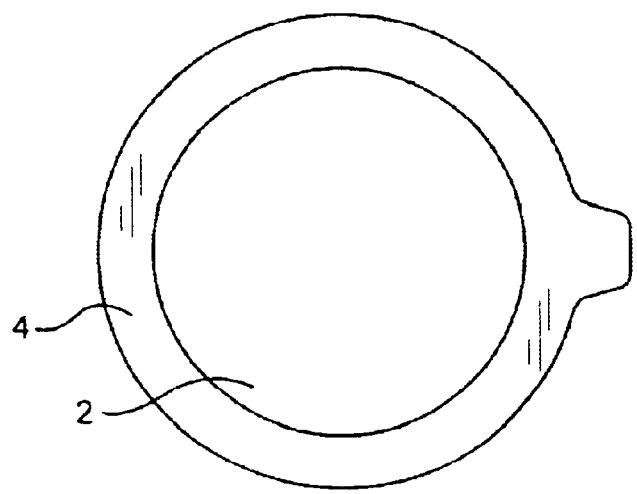
FIG. 3 shows a die cut shape frame of film for a round culture dish, according to a second embodiment.
Figure 4:
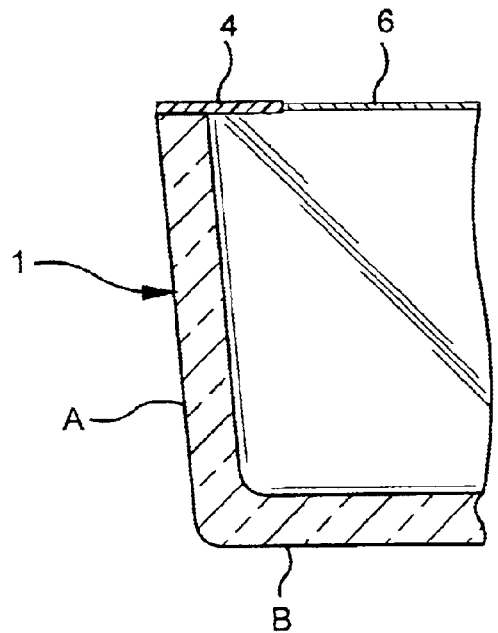
FIG. 4 shows a cross-sectional view of part of a culture dish with the frame and film, according to either FIG. 2 or 3, sealed to a top edge of the dish.
Figure 5:
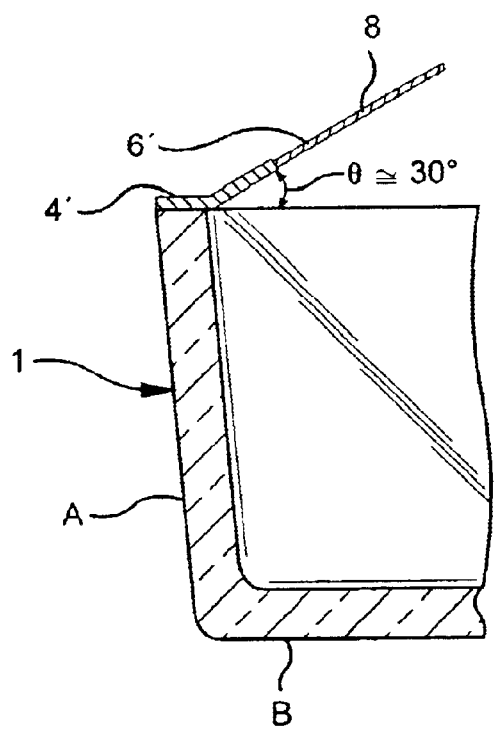
FIG. 5 shows across-sectional view of part of a culture dish with the film, according to either FIG. 2 or 3, attached to a top edge of the dish, and tilted open at about 30° angle relative to the top edge of the dish for easier access to the interior.
Figure 6:
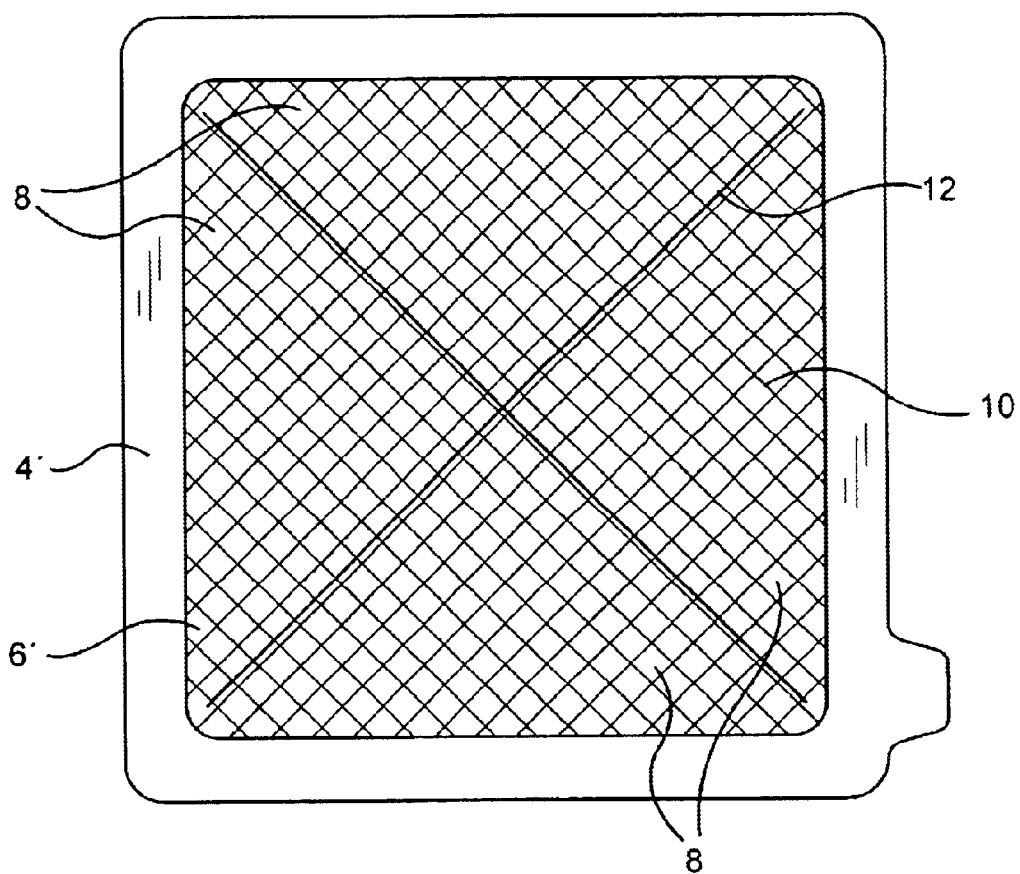
FIG. 6 shows an alternate embodiment of the splash-guard, according to FIG. 2 for a rectilinear culture dish, that incorporates a film extending across the opening of a frame and having a number of ribs or webbing members to provide rigidity. The film is scored with slits for access to the interior of the culture dish.
Figure 7:
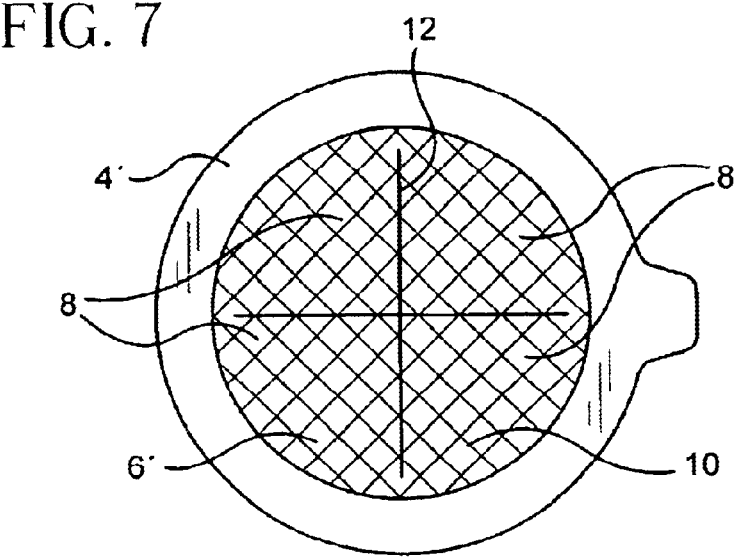
FIG. 7 shows another embodiment similar to that depicted in FIG. 6, for a round culture dish.

As illustrated in FIGS. 2 and 3, the present splash-guard design is made from a semi-rigid film that can be die cut into almost any desired geometry (e.g., circular, square, rectangular, parallelogram, triangular, trapezoidal, and polygonal forms). The splash-guard comprises a frame of film that defines a central aperture 2 around the edge of the open-end of the basin or plate 1. This frame of film is attached, for instance, by heat welding to the top edge of the sidewall A to form a hermetic seal between the splash-guard and plate 1. This hermetic seal keeps fluids from migrating or wicking to the outside and avoids liquid bridges that permit cultured samples to leak out of the culture plate, or other bacteria or undesirable contaminants to come into the plate. The seal, thus, maintains sterility for the plate. The frame forms an angular flange 4, 4' that surrounds the top opening of the culture plate and occupies in part a portion of the periphery of the open-end of the culture plate. As shown in FIG. 4, the flange 4 is positioned at least parallel to plane of the bottom wall B. In most instances this would be about 90 degrees relative to the plane of the sidewall A. (As used herein, an angle "about 90 degrees" may deviate from actual 90 degrees within a range from about 80 to about 95 degrees.) In other instances, it is contemplated that the present invention can have an angle of less than about 90 degrees, so long as the flange or film does not dip significantly into the volume of the plate. In some other possible embodiments, the flange can have an angle greater than 90 degrees, up to about 180 degrees. Preferably, the flange has an angle between about 90 to about 135 degrees relative to an attachment point on the top edge of the culture plate. To fabricate splash-guard designs with an angle greater than 90 degrees, vacuum forming techniques may be employed to mold the film material. In other embodiments, a semi-rigid film 6, 6' covers across the entire open top of the basin or plate. Above the center area of the plate, in the film are perforated two slits 12 in the form an X, which creates four triangular-shaped flaps in the film 6, 6'. According to this embodiment, the four flaps can be folded back over the rest of the film. This action opens the center area of the plate for access to the interior. The flaps, since they are semi-rigid, can also be turned back in place to cover opening of the plate 1.

The film out of which the splash-guard is made can be selected from a variety of materials, including for example, poly(tri-methylene terephthalate), poly-phenylene oxide, Mylar®, polypropylene, or polystyrene co-polymers. Other materials include a thin metallic foil (e.g., aluminum) or heat-sealed film with a layer of polymer serving as the bonding agent. To provide rigidity to the frame, the film can also be strengthened with ribbing 10 or a webbed network 8 within the frame 4, 4' and film 6, 6'. Alternatively, the thickness of the film can be adjusted to the desired rigidity or flexibility. Preferably, the film 6 is clear i.e., transparent), or at least translucent, to enable a user to see the area of the culture plate 1 directly underneath the splash-guard. This feature would be useful to workers when preparing, processing, and observing the culture sample. Preferably, polyesters or any product of a terephthalic acid and a diol, such as poly(ethylene terephthalate), are good materials to use.

The particular orientation and removable attribute of the present splash guard design avoids or prevents many of the issues that are present in current products of like purpose. First, as alluded to before, fixed or permanent splash-guards can hinder access and prevent a clear view of the entire culture surface. Unlike the designs shown in U.S. Pat. No. 5,591,891, which have a baffle that extends inwardly and downwardly at an angle to the sidewall that prevents ready access to regions behind the baffle, the present splash-guard design affords relatively free access to all parts of the culture plate. Even with the splash-guard installed, a user can still reach every part of the culture plate with an instrument, like either a scrapper tool or pipette tip.

Second, no part of the splash-guard design dips down into the volume of the plate where it may come into contact with the liquid. The splash-guard is located on the top edge or rim of the culture plate in at least an orthogonal orientation. This avoids contamination problems associated with capillary uptake of media into nonsterile or inaccessible regions of the plate. With splash-guard designs that are inserted into the plate basin can come into contact with the liquid media, space between the splash-guard and the inside surface of the plate's side wall is very small. Liquid media and cells can become trapped by wicking in between the splash-guard insert and sidewall. Cells can die in between the two surfaces and contaminate the entire plate. With the present splash-guard design, wicking is eliminated. Furthermore, the inventive splash-guard design will greatly reduce the chance for contamination of the sterile contents of the vessel from migration of microorganisms from the outside, nonsterile portions of the vessel. This will help preserve the cultures grown in the vessel for extended periods from loss due to contamination.

Third, although some embodiments of splash-guards or baffles for culture plates are said to be removable, often those designs require a user apply much force to pry off the baffle. This defeats the entire purpose of not to agitate the liquid and cause it to spill out of the culture plate. A splash-guard, like the present invention, in contrast, can be removed without much force or effort. Merely by peeling back the from the top edge of the culture plate in an easy, fluid motion, one does not disturb the liquid media in the container. One can merely exert a minor force of between about 50 to about 1500 grams to peal back the splash guard film.

To summarize, the present invention encompasses an article of manufacture, and methods for its fabrication and use. The article is fluid receptacle for microorganism cultures, also known as a culture dish. The culture dish comprises an open-ended container with a bottom wall, at least one sidewall extending upwardly from the bottom wall, and an angular splash-guard. The splash-guard comprises a frame that defines a central aperture. The frame has an inwardly extending flange, which projects over a peripheral portion of the bottom wall. The frame is made of a semi-rigid material, forms a hermetic seal with a top edge of the sidewall, and is removably attached to the top edge of the sidewall. The splash-guard or frame comprises a polymer film made of either polyester or a reaction product of a terephthalic acid and a diol. Metallic foils that are sealable may also be used. The splash-guard is strengthened with ribs or a webbed network. In one embodiment, heat welding is used to form a hermetic seal between the splash-guard and the top edge of the sidewall. Means of bonding include, but are not limited to hot plate welding, impulse welding, ultrasonic welding, or pressure sensitive tape, and the like. This applies also to metallic foil or film embodiments. The splash-guard, however, can be conveniently peeled or released from the container with a pull-tab. The splash-guard can conform to conventional culture-plate lid configurations and fits easily under a lid when the culture dish is covered. The frame of the splash-guard has a shape that is selected from the group consisting of circular, square, rectangular, parallelogram, triangular, trapezoidal, and polygonal forms. Additionally, the frame is oriented parallel to the plane of the bottom wall, or at an angle of about 90 degrees or greater relative to the sidewall of the container.

As a method for fabricating a culture dish, the present invention comprises a number of steps. First is to form a vessel having a bottom wall, at least one sidewall extending upwardly from said bottom wall, and an open top-end defined by an upper rim of the sidewall. Second is to die cut a polymer film into a geometry and size corresponding to the shape of the open top-end of the culture dish. Third is to form a removable and hermetic seal between the polymer film with the upper rim of the sidewall. The polymer film is sealed to the upper rim of the sidewall with an amount of pressure of about 20 psi to about 100 psi depending on the material. Pressures of about 40 psi to about 60 psi are more common.

A method for using the culture dish comprises: providing a culture dish having an open top-end with a removable splash-guard hermetically sealed to a top edge of a sidewall; loading a liquid medium into said cell culture dish; depositing an inoculum onto said cell culture dish; processing said inoculum; and peeling said splash-guard off of said cell culture dish. The polymer film can be removed from the culture dish with an amount of force of at most about 1500 grams or less, or of at least 50 grams or more. Preferably, the removal force is between about 100-200-700 grams, more preferably about 150 grams. Standard liquid culture media can be used with this device. Alternatively, semi-solid media can be used through gelling the liquid with an agent such as agar or agarose. The inoculum can be selected from any kind of bacterium, cell, virus, or other microorganisms.

Although the present invention has been described in detail above, various changes and modifications will be apparent to those skilled in the art. Therefore, unless such changes and modifications otherwise depart from the scope of the present invention, as described herein and defined by the following claims, they are to be construed as included.

We claim:

1. A culture dish comprising:
an open-ended container with a bottom wall, at least one sidewall extending upwardly from the bottom wall, and
a splash-guard, which comprises a frame of film that defines a central aperture;
said frame having a flange which extends from said sidewall partially over a peripheral portion of said bottom wall.

2. The culture dish according to claim 1, wherein said frame is made of a semi-rigid material.

3. The culture dish according to claim 1, wherein said splash-guard forms a hermetic seal with a top edge of said sidewall.

4. The culture dish according to claim 3, wherein said hermetically seals is formed by heat welding said splash-guard to the top edge of the sidewall.

5. The culture dish according to claim 1, wherein said splash-guard is detachable from said top edge of the sidewall.

6. The culture dish according to claim 5, wherein said splash-guard is peelably released from said container.

7. The culture dish according to claim 1, wherein said splash-guard is made of a polymer material.

8. The culture dish according to claim 1, wherein said splash-guard is made of a polyester.

9. The culture dish according to claim 1, wherein said splash-guard is made of polymer product of a terephthalic acid and a diol.

10. The culture dish according to claim 1, wherein said splash-guard comprises a metallic film.

11. The culture dish according to claim 1, wherein said splash-guard is strengthened with ribs.

12. The culture dish according to claim 1, wherein said splash-guard contains a webbed network.

13. The culture dish according to claim 1, wherein said splash-guard further comprises a retractable film that covers a portion of said central aperture.

14. The culture dish according to claim 1, wherein said splash-guard has a pull-tab.

15. The culture dish according to claim 1, wherein said splash-guard conforms to a conventional culture plate lid configuration and fits easily under a lid when the culture dish is covered.

16. The culture dish according to claim 1, further comprises a sheet of film having openings therein, which extends over said central aperture.

17. The culture dish according to claim 1, wherein said frame of said splash-guard is either oriented parallel to the plane of said bottom wall, or at an angle of about 90 degrees or greater relative to said sidewall of the container.

18. A fluid receptacle for cell cultures comprising:
a container with an open top-end;
a splash-guard having a frame of film, made of a semi-rigid material, that defines a central opening, said frame is hermetically sealed to but detachable from a rim of said container near said open top-end.

19. The fluid receptacle according to claim 18, wherein said frame has flanges that extend inwardly from said rim of said container either parallel to the plane of said bottom wall, or at an angle of about 90 degrees or greater relative to a sidewall of said container.

20. The fluid receptacle according to claim 18, further comprising a film sheet having openings therein which extends over said central opening.

21. The fluid receptacle according to claim 18, wherein said splash-guard is strengthened with ribs.

22. The fluid receptacle according to claim 18, wherein said splash-guard contains a webbed network.

23. The fluid receptacle according to claim 18, wherein said ribs or webbed network forms part of said film sheet.

24. The fluid receptacle according to claim 18, wherein said splash-guard comprises a polymer film.

25. The fluid receptacle according to claim 18, wherein said splash-guard comprises a metallic foil.

26. The fluid receptacle according to claim 14, wherein said splash-guard conforms to a lid configuration and fits easily under a lid when the container is covered.

27. A method for fabricating a vessel, the method comprising:
   a) providing a container having a bottom wall, at least one sidewall extending upwardly from said bottom wall, and an open top-end defined by an upper rim of said sidewall;
   b) cutting a film into a geometry and size corresponding to the shape of said open top-end of the container to form a frame, which defines a central aperture; and
   c) forming a hermetic seal between said film and the upper rim of the sidewall.

28. The method according to claim 27, wherein said film is affixed to the upper rim of the sidewall with a section of said film extending over a portion of the bottom wall.

29. The method according to claim 27, wherein said film made of a semi-rigid material.

30. The method according to claim 27, further comprises extending a sheet of film having openings therein over said central aperture.

31. The method according to claim 27, wherein said frame or said sheet of film is strengthened with either ribs or a webbed network.

32. The method according to claim 27, wherein said film is made of a polymer.

33. The method according to claim 27, wherein said film comprises a metallic foil.

34. The method according to claim 27, wherein said frame is heat-welded to said upper rim.

35. The method according to claim 27, wherein said film is sealed to said upper rim of the sidewall with an amount of pressure of about 20 psi to about 100 psi.

36. The method according to claim 27, wherein said film is detachable from said upper rim.

37. The method according to claim 27, wherein said film is detached from said culture dish using an amount of force of at about 700 grams or less.

38. The method according to claim 27, wherein said film is detached from said culture dish using an amount of force of at least 50 grams or more.

39. The method according to claim 27, wherein said film conforms to the configuration of a conventional cell-culture-dish lid and fits easily under a lid when the culture dish is covered.

40. The method according to claim 27, said frame of film is cut into a shape that is selected from the group consisting of circular, square, rectangular, parallelogram, triangular, trapezoidal, and polygonal forms.

41. A method for using a culture dish, the method comprising:
   a) providing a culture dish having an open top-end with a removable splash-guard hermetically sealed to a top edge of a sidewall, said splash-guard comprising a frame of film that defines a central aperture;
   b) loading a liquid medium into said culture dish;
   c) depositing an inoculum onto said culture dish;
   d) processing said inoculum; and
   e) peeling said splash-guard off of said culture dish.

42. The method according to claim 41, wherein said liquid medium gels.

43. The method according to claim 41, wherein said inoculum is a selected from the group consisting of bacteria, cells, viruses, or other microorganisms.

* * * * *